United States Patent
George et al.

(10) Patent No.: US 10,272,206 B2
(45) Date of Patent: *Apr. 30, 2019

(54) LEUPROLIDE INJECTION

(71) Applicant: Sun Pharmaceutical Industries Limited, Andheri East, Mumbai (IN)

(72) Inventors: Alex George, Vadodara (IN); Prashant Kane, Vadodara (IN); Subhas Bhowmick, Vadodara (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 73 days.

This patent is subject to a terminal disclaimer.

(21) Appl. No.: 15/597,523

(22) Filed: May 17, 2017

(65) Prior Publication Data

US 2017/0252517 A1    Sep. 7, 2017

Related U.S. Application Data

(63) Continuation of application No. 14/172,384, filed on Feb. 4, 2014, now Pat. No. 9,656,023, which is a (Continued)

(30) Foreign Application Priority Data

Apr. 30, 2012    (IN) .......................... 1349/MUM/2012

(51) Int. Cl.
*A61M 5/315*    (2006.01)
*A61K 9/00*    (2006.01)
(Continued)

(52) U.S. Cl.
CPC ....... *A61M 5/31593* (2013.01); *A61K 9/0019* (2013.01); *A61K 9/08* (2013.01);
(Continued)

(58) Field of Classification Search
CPC .......... A61M 5/31593; A61M 5/31533; A61M 5/3155; A61M 5/31551; A61M 5/31553;
(Continued)

(56) References Cited

U.S. PATENT DOCUMENTS

2003/0186892 A1    10/2003    Taneja

FOREIGN PATENT DOCUMENTS

| EP | 0496141 A1 | 7/1992 |
| WO | 03082319 A1 | 10/2003 |
| WO | 2010115762 A1 | 10/2010 |

OTHER PUBLICATIONS

RxList the Internet Drug Index, Lupron Injection, Retrieved from the Internet: http://www.rxlist.com/lupron-drug/indications-dosage.htm; pp. 2; Date Mar. 3, 2011.
(Continued)

*Primary Examiner* — Bhisma Mehta
*Assistant Examiner* — James D Ponton
(74) *Attorney, Agent, or Firm* — Sughrue Mion, PLLC

(57) ABSTRACT

The present invention provides a sterile solution comprising leuprolide acetate in a pharmaceutically acceptable vehicle, wherein solution is present as a reservoir in a multiple dose pen injection device, the device being adapted to subcutaneously inject a portion of the said reservoir in a single daily dose and further being adapted to provide multiple portions of solution said while the reservoir remains sterile.

4 Claims, 2 Drawing Sheets

Related U.S. Application Data continuation of application No. 13/873,325, filed on Apr. 30, 2013, now abandoned.

(51) Int. Cl.
  *A61K 38/09* (2006.01)
  *A61K 47/10* (2017.01)
  *A61K 9/08* (2006.01)
  *A61M 5/32* (2006.01)
  *A61M 5/31* (2006.01)

(52) U.S. Cl.
  CPC .............. *A61K 38/09* (2013.01); *A61K 47/10* (2013.01); *A61M 5/3202* (2013.01); *A61M 5/3146* (2013.01); *A61M 5/3155* (2013.01); *A61M 2005/3126* (2013.01)

(58) Field of Classification Search
  CPC . A61M 5/31555; A61K 9/0019; A61K 38/09; A61K 47/10
  See application file for complete search history.

(56) References Cited

OTHER PUBLICATIONS

European Search Report Corresponding to European Application No. 13165890.8-1460, dated Aug. 19, 2013.
Eon Labs, Inc. Leuprolide Acetate-Leuprolide acetate injection, solution, distributed by Eon Labs, Inc.,; Revised Jan. 2011; pp. 1-7.

LEUPROLIDE INJECTION

This application is a continuation of application Ser. No. 14/172,384, filed Feb. 4, 2014, which is a continuation of application Ser. No. 13/873,325 filed Apr. 30, 2013 now abandoned, which claims benefit to Indian Patent Application No. 1349/MUM/2012, filed Apr. 30, 2012, in the Indian Intellectual Property Office, the disclosures of each of which are incorporated herein by reference in their entirety.

FIELD OF INVENTION

This invention relates to a sterile solution of leuprolide acetate present as a reservoir in a multiple dose pen injection device adapted to administer a portion of the reservoir in a single daily dose.

BACKGROUND OF INVENTION

Leuprolide acetate is a synthetic nona-peptide analog of naturally occurring gonadotropin releasing hormone (GnRH or LH-RH). It is used to treat prostatic cancer in adults and in the treatment of children with central precocious puberty. Presently it is available in the market as an aqueous solution (Lupron®) intended for subcutaneous injection and is available in a 2.8 ml multiple-dose vial containing leuprolide acetate (5 mg/ml) and benzyl alcohol as a preservative (9 mg/ml). The daily recommended dose of leuprolide acetate is 1 mg (200 microliter) administered as a single daily subcutaneous injection. The label indicates that adherence to daily drug administration schedules must be accepted for successful therapy. Further, successful basic therapy with leuprolide acetate requires that the patient be administered a suitable dose of leuprolide acetate daily over a period of six months.

The approved product is available as a 14 Day Patient Administration Kit with 14 disposable syringes and 28 alcohol swabs. The package insert of the approved product provides directions to the user that when the drug level gets low, special care needs to be taken to hold the bottle straight up and down and to keep the needle tip in liquid while pulling back on the plunger. In an attempt to try to get every last drop out of the bottle, there is an increased possibility of drawing air into the syringe and getting an incomplete dose and attendant health risks. The level of the dose is accordingly dependent on the user correctly carrying out the enclosed instructions. In principle, leuprolide acetate can be administered only parenterally and not orally. Further administration of a large amount of active substance solution (e.g. up to 0.2 ml in the case of a certain dosage as with Leuprolide acetate) under the skin every day, may be especially difficult to convey to patients, especially children and cancer patients. Children, in particular may exhibit a certain aversion to taking injection by conventional syringes moreover because considerable injection pain is associated with large volume injections. Cancer patients who are already in a state of high level of pain cannot tolerate even a slight increase in the level of pain. Moreover, it is available in 2.8 ml multiple-dose vial with 14 disposable syringes for daily subcutaneous injection of single doses of 1 mg leuprolide acetate in 0.2 ml of solution, over 14 days. Moreover, the prior art involves withdrawal of the drug solution from a separate storage container. It is apparent that the approved product® has several drawbacks such as patient non-compliance, possibility of error in withdrawing solution from syringes, and aversion about use of needle and syringe. Further, since the dosing regimen involves daily subcutaneous administration, patient compliance may be a particular concern. Therefore, there lies a requirement for an improved leuprolide acetate subcutaneous injection solution and a method of daily administering leuprolide acetate which takes care of the enumerated problems with the known product and provides an improved effective, user friendly leuprolide therapy. The present invention precisely provides an improvement. The improvement avoids the cumbersome kit of the prior art product, Lupron® and can delivery daily subcutaneous injections of single doses of 1 mg leuprolide acetate in a smaller volume of solution to over more than 14 days, preferably up to 28 days while maintaining sterility of the leuprolide acetate solution. An additional advantage of the preferred embodiments of the present invention is that in a single daily dose a lower amount of preservative is delivered. Additionally, the use of a multiple dose pen device allows flexibility in choosing different volumes of injection by the patient himself with ease, without concern about the accuracy in withdrawing volumes which would be otherwise present a major concern in case of the vial type of product for example as available under the brand name of Lupron®.

SUMMARY OF THE INVENTION

The present invention provides a sterile solution comprising leuprolide acetate in a pharmaceutically acceptable vehicle, wherein the solution is present as a reservoir in a multiple dose pen injection device, the device being adapted to subcutaneously inject a portion of the said reservoir in a single daily dose and further being adapted to provide multiple portions of said solution while the reservoir remains sterile.

BRIEF DESCRIPTION OF FIGURES

The invention is illustrated by the accompanying figures in which:

FIG. 2(*b*) shows a perspective view of a multiple dose pen injection according to the invention being primed for use.

In particular, FIG. 1 shows the multiple dose pen injection device according to one embodiment of the present invention. The figure depicts a cap (1) that covers a pre-filled medicament cartridge and a dose dialing facility (2). The dose dialing facility has a dose dial with varied markings (3) along with a dose set knob (4) that allows the user to select the desired dose and a dose release button (5) which is pressed to inject the selected dose. In FIG. 1, two markings visible in the dose dial include '0' and 'P' wherein '0' depicts the initial starting position and 'P' stands for priming unit which is to be set for priming of multiple dose pen injector.

FIG. 2(*a*) shows the prior art 'conventional syringe-vial assembly' used to administer the marketed product—Lupron®. The figure depicts a conventional syringe (2-1) having a plunger and a needle (2-2), the needle being inserted in a vial (2-3) through a rubber stopper (2-4). The Figure represents the process of withdrawal of the medicament liquid from the vial by use of a conventional syringe. It is evident that the approved product available in the market (Lupron®) makes use of a conventional syringe-vial assembly wherein administration of medicament involves manual withdrawal of the drug solution from a vial with the help of a conventional syringe followed by administration to the patient using the syringe. Such delivery method is associated with several drawbacks such as patient non-compliance, possibility of errors in withdrawing solution from syringes and aversion about use of needle and syringe. The pack insert of the approved marketed product (Lupron®) emphasizes the criticality of using the product correctly. For instance, the pack insert direct the user that when the drug level gets low, special care needs to be taken to hold the bottle straight up and down and to keep the needle tip in liquid while pulling back on the plunger. In an attempt to try to get every last drop out of the bottle, there is an increased possibility of drawing air into the syringe and getting an incorrect/incomplete dose.

FIG. 2(b) shows a multiple dose pen injection device according to one embodiment of the present invention depicting the process of priming of the multiple dose pen injection device prior to first use, wherein the priming is conveniently done by adjusting the dose selection knob to marking P in dose dial followed by pushing the release button until a stream of medication oozes out from the needle to ensure the removal of any air bubble inside the cartridge. It is to be noted that the priming can be done simply by adjusting the dose selection knob to marking P in dose dial followed by pushing the release button until a stream of medication oozes out from the needle to ensure the removal of any air bubble inside the cartridge.

DETAILED DESCRIPTION OF THE INVENTION

Figure 1:
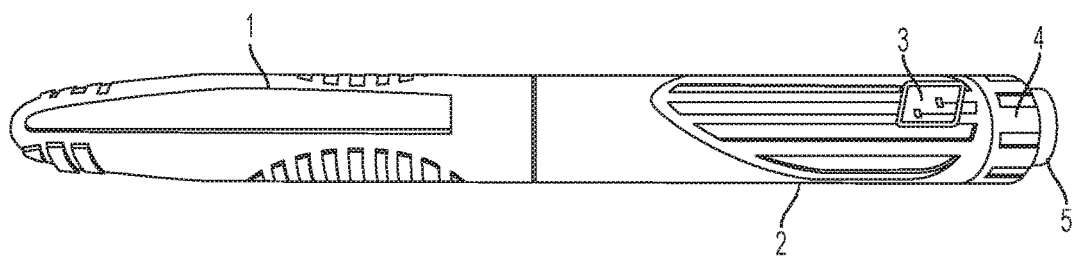
FIG. 1 shows a perspective view of a multiple dose pen injection device according to the invention.
Figure 2:
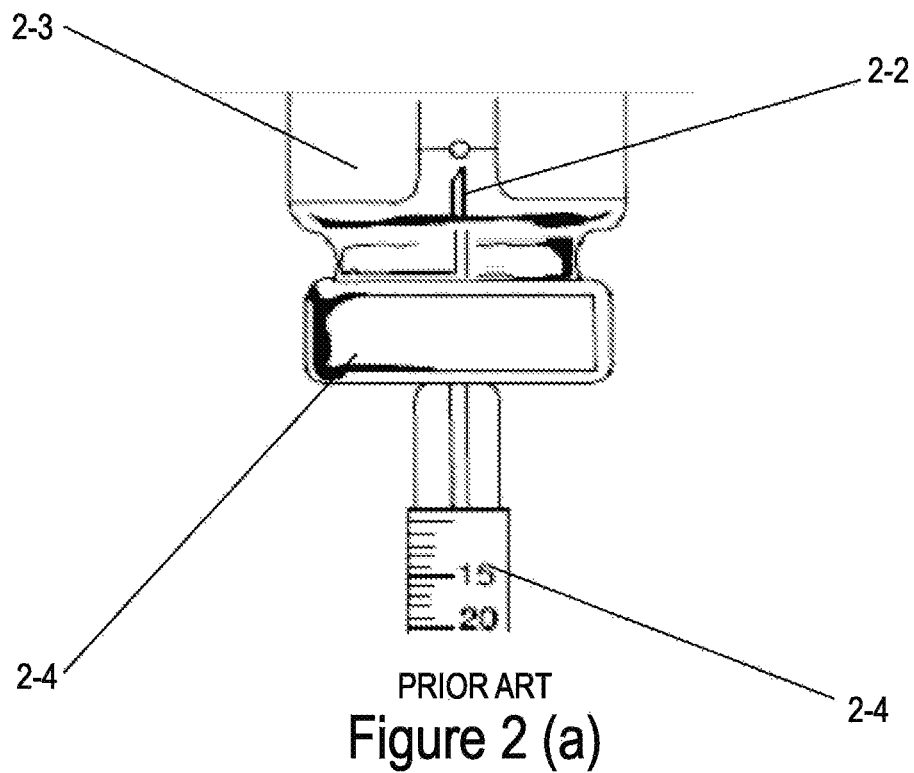
FIG. 2(*a*) shows a perspective view of a part of a multiple dose pen injection device according to the prior art.
Figure 2:
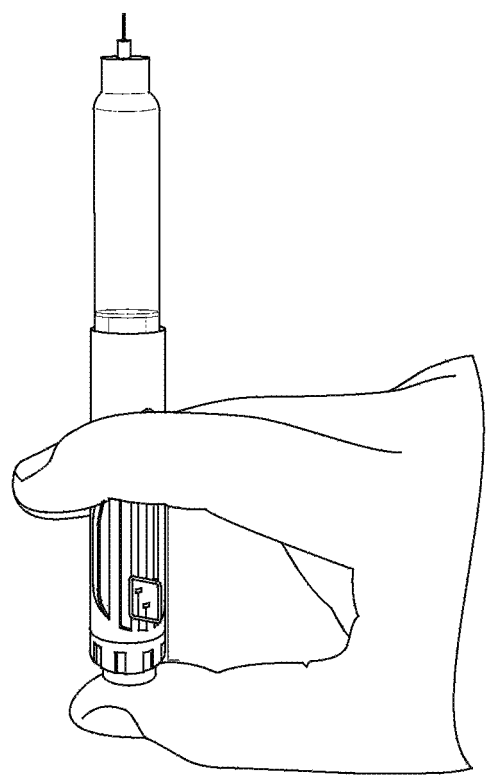

The term 'multiple dose pen injection device' as used herein means an injection assembly which can house a reservoir of a multiple, sterile, doses of leuprolide acetate in solution. Preferably the reservoir is in a cartridge. Further the multiple dose pen injection device suitably includes a dose dialing facility that allows the user to select and inject a desired dose of leuprolide acetate. The device may include an injection assembly in which the reservoir of leuprolide acetate is in a cartridge which is in-built in the multiple dose pen injection device and it does not involve the withdrawal of the drug solution from a separate storage container as is the case in conventional syringe-vial assembly.

Suitably, the multiple dose pen injection device according to one embodiment of the present invention, comprises a cap covering a cartridge holder, that holds the cartridge filled with reservoir of sterile, preserved leuprolide solution and a dose dialing facility having a dose dial with a range of markings visible through a dose window and a dose set knob that allows the user to select the desired dose. In one embodiment, the dose dial can have marking '0' depicting the initial starting position, marking 'P' (250 µg) for priming, marking 500 for dosing 500 µg drug and marking 1000 for dosing 1000 µg drug. Alternatively, the dose dial can have a marking in which a dose of leuprolide in milligrams can be expressed instead of the volume of injection. For example, '0.0 mg' depicts the initial starting position, marking 'P' for priming the dose and marking 1.0 mg for dosing 1.0 mg drug. In a preferred embodiment, the 'multiple dose pen injection device' does not include any mechanics to create a force or suction such as use of a plunger.

The sterile solution of the present invention comprises preservative in amounts sufficient to maintain sterility of the solution in the multiple dose pen injection device, throughout the shelf life of the product, which may be exposed to repeated multiple injections. This is because it is possible that the antimicrobial preservative concentration in a given preparation may decrease during the product's shelf life. USP35-NF30 Page 154-56 states that a quantitative label statement of the preservative content is not intended to mean that the labeled quantity is retained during the shelf life of the product; but it is important that the lowest permissible concentration of the label amount of preservative is retained during the shelf life.

Desirably, the sterile solution comprises leuprolide acetate in a pharmaceutically acceptable vehicle, wherein the solution is administrable directly from a multiple dose pen injection device. Preferably, all the ingredients or excipients of the sterile solution are in the dissolved or soluble state and there is no particulate matter. Particularly, the sterile solution of the present invention does not include any material that may exhibit a deposit or sustained release effect to the leuprolide acetate upon injection or as such. That is, the sterile solution of the present invention, is essentially suitable for daily administration for consecutive days for a period of therapy, such as a few months, for instance 6 to 12 months. According to the present invention, the sterile solution comprises leuprolide acetate in an amount ranging from 1 mg per milliliter to 50 mg per milliliter, particularly, from about 5 mg to 20 mg per milliliter, preferably 10 mg per milliliter of the solution. In one specific embodiment, the leuprolide acetate is present in an amount of 10 mg per milliliter of the solution. The sterile solution is suitably administered in a dose having a volume from 25 µL to 200 µL. Preferably, the lueprolide acetate is present in the multiple dose pen injection device as a reservoir containing multiple doses. The reservoir preferably contains 14 to 42 doses, for example 28 doses.

In another aspect of the invention, there is provided a multiple dose pen injection device comprising a reservoir of a sterile solution comprising leuprolide acetate and a preservative, the device being adapted to provide a portion of the reservoir directly from the multiple dose pen injection device in a single subcutaneous injection, said portion comprising leuprolide in a pre-determined dose and the device further being adapted to provide multiple portions of the said solution while the reservoir remains sterile.

The present invention also provides a multiple dose pen injection device comprising a sterile solution of leuprolide acetate in a pharmaceutically acceptable vehicle wherein the sterile solution is present as a reservoir, the device being adapted to subcutaneously inject a portion of the said reservoir in a single daily dose and further being adapted to provide multiple portions of said solution while the reservoir remains sterile. Thus, suitably, the sterile solution is essentially a multidose preparation, that is, the sterile reservoir of the solution that can be used for delivering multiple doses. Preferably, a reservoir of the sterile solution is present in the multiple dose pen device and a portion of that reservoir is withdrawn for each administration. The portion suitably contains a desired dose of the leuprolide acetate. The sterile solution of the present invention is not meant for single dose administration and therefore, not terminally sterilized. Since the multiple dose pen injection device of the present invention is for multiple dose injections, integrity of the seal of the multiple dose pen injection device may be compromised during the multiple uses. The sterile solution of the present invention includes preservative in amounts sufficient to maintain sterility of the solution in the multiple dose pen injection device, throughout the shelf life of the product, which may be exposed to repeated, daily multiple injections. Suitable preservatives for the solution includes but are not limited to, benzyl alcohol, m-cresol, phenol, methyl parabens, propylparaben, butylparaben, chlorbutanol, thiomersal, phenylmercuric salts, and the like. For instance, when the solution contains benzyl alcohol as the preservative, it is present in an amount sufficient to maintain sterility of the solution in the multiple dose pen injection device, throughout the shelf life of the product, which may be exposed to repeated multiple injections. The amount of benzyl alcohol may range from about 9 mg per milliliter to about 15 mg per milliliter of the solution. Preferably, in one embodiment, the sterile solution comprises benzyl alcohol in amounts ranging from 9 mg per milliliter to 11.25 mg per milliliter. In one specific embodiment, the sterile solution of the present invention comprises 5 mg per milliliter of leuprolide acetate, and about 9 mg per milliliter of benzyl alcohol. In another embodiment, the sterile solution comprises 10 mg per milliliter of leuprolide acetate and at least 11.25 mg per milliliter of benzyl alcohol per milliliter of the solution. In another embodiment, the sterile solution comprises 20 mg per milliliter of leuprolide acetate and 15 mg per milliliter of benzyl alcohol per milliliter of the solution. In a most preferred embodiment, the sterile solution comprises 10 mg per milliliter of leuprolide acetate and 11.25 mg per milliliter of benzyl alcohol per milliliter of the solution.

Preferably, the amount of preservative per mg dose of leuprolide acetate was much lower as compared to the approved product (Lupron®). In one embodiment, the amount of benzyl alcohol injected per dose of leuprolide acetate is 1.125 mg as compared to 1.8 mg of benzyl alcohol present in Lupron®. The inventors have surprisingly found that sterility may be maintained in-spite of having a reduced amount of preservative as compared to the known commercial product.

In one embodiment, the multiple dose pen injection device comprises a cartridge filled with a solution of leuprolide acetate, comprising benzyl alcohol as a preservative. The preservative containing solution is aseptically filtered (through 0.45 micron PVDF pre-filter and 0.2 micron PVDF filter) and filled in pre-sterilized cartridges aseptically under laminar flow. Suitably, there is no terminal sterilization step involved in the process. As the solution is intended for use as a multiple dose, it comprises leuprolide acetate along with a preservative agent to keep the sterility maintained while being used multiple times throughout the shelf life of the product. Apart from a preservative, the pharmaceutically acceptable vehicle may comprise a buffer or isotonicity agent. Suitably, the solution does not contain any material that can retard release of leuprolide acetate, upon injection or as such. Such materials include, but are not limited to, polymers which may be synthetic or biodegradable, gelling or non-gelling, ion exchange resins and the like. The pH of the solution is suitably adjusted to a pH range of 4.5 to 6.5. The pH may be adjusted using an acid, for example 10% acetic acid. However, it is possible to use a buffer system to maintain the pH range. Suitable buffers that may be used include, but are not limited to acetate buffer, lactate buffer, citrate buffer, gluconate buffer, tartrate buffer, phosphate buffer and the like. Examples of tonicity adjusting agents include, but are not limited to, sodium chloride, mannitol, lactose, sucrose, maltose, trehalose and the like and mixtures thereof. The sterile solution may optionally comprise a chelating agent such as disodium-EDTA and the like.

Generally, it is known that the preservative efficacy test (PET) is performed to evaluate the performance of a preservative. Such tests are described in literatures, such as for eg. United States Pharmacopoeia. The solution being suitable for multiple dosing, the PET was performed. It was surprisingly found that at a higher concentration of leuprolide acetate that is at 10 mg per ml strength, 11.25 mg per ml of benzyl alcohol was sufficient to preserve the solution. This finding was unexpected because for a known leuprolide solution for subcutaneous administration having 5 mg per ml of leuprolide acetate, 9 mg per ml of benzyl alcohol is used. However, in one embodiment, when the concentration of leuprolide acetate in the solution was increased two fold (to 10 mg/ml), corresponding two fold increase in concentration of the preservative, for instance, benzyl alcohol (18 mg/ml i.e. double of 9 mg/ml) was unexpectedly not required. A concentration of 11.25 mg per ml, instead of 18 mg/ml (double of 9 mg/ml of benzyl alcohol) was surprisingly found to be sufficient to preserve the solution during its shelf life. This is particularly advantageous as the amount of preservative in the solution of the present invention injected daily, as compared to known leuprolide subcutaneous solutions available in the regulated markets, would be reduced, (from 1.8 mg/dose to 1.125 mg/dose) apart from reduction of dose volume to half (from 0.2 ml to 0.1 ml).

Thus, the present invention can be said to provide an improvement in a method of administering leuprolide to a human, said improvement comprising, (a) considering a method of administering leuprolide to a human subject by administering a solution containing 5 mg/ml of leuprolide acetate and preservative at an effective concentration (b) providing a sterile solution containing at least 10 mg/ml of leuprolide acetate and preservative at concentration ranging from the same effective preservative concentration as in (a) to 25% increased preservative concentration as in (a)

(c) administering the effective dose of leuprolide subcutaneously whereby the patient receives an effective dose of leuprolide while being exposed to a lower level of a preservative as compared to the approved marketed product. In a preferred embodiment, the preservative comprises benzyl alcohol. The solution preferably comprises leuprolide acetate at a concentration of 10 mg/ml and benzyl alcohol at a concentration of 11.25 mg/ml.

The invention also provides a method of maintaining the sterility of a reservoir of a leuprolide acetate solution in a multiple dose pen injection device for subcutaneous injection of the solution to a subject in multiple doses from the reservoir, the method comprising providing in a multiple dose pen injection device a solution containing at least 10 mg/ml of leuprolide acetate and a preservative at concentration ranging from the concentration at which 5 mg/ml of leuprolide acetate is maintained sterile to 1.25 times that concentration of the preservative.

The sterile solution of the present invention being a multidose preparation, it needs to maintain sterility during its shelf life that is while being used. Thus, the solution of the present invention in the multiple dose pen injection device, was subjected to in-use stability testing. The routine procedure provided by United States Food and Drug Administration (FDA), United States Pharmacopoeia (USP) and the European Pharmacopoeia (EP) are followed to evaluate the sterility. The tests are PET (preservative Efficacy tests), sterility and BET (Bacterial Endotoxin Test). It was surprisingly observed that lower quantity of a preservative like benzyl alcohol provided satisfactory preservative efficacy throughout the shelf life of the product. It was effective in low concentration even when the concentration of the drug in the solution is increased two fold without requiring the concentration of the preservative to be increased proportionately. The preservative maintained its potency and it was observed that it is non reactive with the components of the container or closure system.

An in-use shelf-life is intended to provide assurance of the appropriate quality of the product throughout its use, thereby ensuring the safety and efficacy of the product. A product used outside its in-use shelf-life may have insufficient levels of the active substance and this may lead to inefficacy (or in some cases contribute to the development of resistance), or it may contain harmful levels of degradation products, or it may be contaminated with micro-organisms which would further challenge a patient whose health may already be compromised. The in-use shelf-life specified depends on the product, in particular its physical, chemical and microbiological characteristics. The in-use shelf-life is generally 28 days, however it may be less than this, for example if the active substance is prone to degradation following exposure to the atmosphere, or it may be longer than this, for example for a product which is very stable and which will not support the growth of micro-organisms (like some non-aqueous/oily injections). The European Union's EMEA has laid down clear guidance on in-use stability testing of Human Medicinal Products (CPMP/QWP/2934/99), wherein it is mentioned that the maximum in-use shelf-life for aqueous preserved sterile products and non-aqueous sterile products after first opening or following reconstitution, should not normally exceed 28 days. Additionally, the European Pharmacopoeia includes a test designed to study the effective use of an antimicrobial preservative system in a medicine. This test is used for human and veterinary medicines and is a 28 day test. The test holds further significance due to the fact that preservative action/concentration of most preservatives added to preserve the multi-dose sterile products may diminish during the shelf life of the product. US Pharmacopoeia, under USP<341> mentions that it is a Pharmacopoeia requirement that the presence and amount of preservative agent(s) be declared on the label of the container and it must be demonstrated that the declared agent does not exceed the labeled amount by more than 20% of the labeled amount. The concentration of an antimicrobial preservative added to a multiple-dose or single-dose parenteral, otic, nasal, and ophthalmic preparation may diminish during the shelf life of the product. Because it is recognized that the antimicrobial preservative concentration in a given preparation may decrease during the product's shelf life, the manufacturer shall determine the lowest level at which the preservative is effective, and the product should be so formulated as to assure that this level is exceeded throughout the product's shelf life.

It is clear that during development of multi-dose sterile products it is necessary to carry out in-use studies to prove that a product remains physically and chemically stable and sterile during the in-use period. The leuprolide solution of the present invention was subjected to these in-use stability and sterility tests. The details of these tests carried out on the sterile solutions of the present invention are presented in the upcoming examples. It was surprisingly observed that the sterile solutions of the present invention complied with all the limits and remained physically & chemically stable and sterile throughout the storage and in-use shelf-life of the product. It was surprisingly found that despite presence of double strength solution of leuprolide acetate compared to the marketed product, the preservative (benzyl alcohol) used in an amount (11.25 mg/ml) less than double the amount (18.0 mg/ml) of the marketed product, maintained proper physical and chemical stability as well as sterility throughout the in-use shelf life of the product. The results of the in-use stability testing are tabulated in Table 3 & 4.

Additionally, storage stability testing of the solution of the present invention was performed and it was observed that the solution stored in the multiple dose pen injection device when kept at room temperature or accelerated stability condition such as 40° C./75% RH for 3 months, remained stable, in terms of both the assay of leuprolide as well as assay of benzyl alcohol. The results of the storage stability testing are tabulated in Table 5.

According to one embodiment, the sterile solution is present in a kit wherein each 100 microliters of solution delivers 1000 µg of leuprolide acetate and thus, the multiple dose pen is sufficient for 28 doses. This is particularly advantageous over the approved product which can cater only 14 doses in one kit. However, it is possible to present lesser or larger volumes of the solution for lower volume of injections per day. The multiple dose pen injection device used to deliver the sterile solution of present invention can be provided in variable dose volumes ranging from 10 µL to 200 µL with desired dose dialing facility and appropriate markings in the dose dial indicating dose in µg. In one embodiment, the multiple dose pen injector device includes a dose dialing facility with markings of 0, 250, 500, 750, 1000 indicating dose in µg such that the desired dose can be administered through variable volumes ranging from 10 µL to 200 µL, preferably 25 µL to 100 µL. Alternatively the markings on the dose dial can be represented in terms of mg dose, wherein the markings may include '0.0 mg' and '1.0 mg' representing the initial position and 1.0 mg dosing position respectively. The multiple dose pen injection device of the present inventions provides accuracy of dose delivery and ease of use for self-injection. In one preferred embodiment, the multiple dose pen injector device include markings '0.0 mg' 'P' and '1.0 mg' in the dose dial wherein the marking '0.0 mg' represents the initial starting position, marking 'P' is for priming the dose and marking '1.0 mg' is for dosing 1.0 mg drug.

To operate the multiple dose pen injection device for administering the solution, the user has to attach a new needle on the tip of the cartridge holder, prime the multiple dose pen prior to first use, select the dose and inject the leuprolide solution by pushing the release button. The dose dialing facility enables the priming of multiple dose pen injector prior to first use, where the dose set knob is set to the appropriate priming unit (P) on the dose dial and the pressing of release button until a stream of medication oozes out from the needle to ensure the removal of any air bubble inside the cartridge. Once the priming is done, the dose to be administered is selected on the dose dial and the leuprolide solution is injected by pushing the release button.

In one embodiment, the multiple dose pen injector employed may include design features such as for last-dose management such that once the last full dose is delivered the remaining dose cannot be delivered. This additional safety features prevents delivery of insufficient last/remaining dose, thus preventing users from receiving incomplete doses. In one embodiment, the multiple dose pen injector device may include a design feature such that in case if the user by mistake turns the dose set knob past the required dose, the same can be corrected by simply turning the knob anti-clockwise to the correct marking. Further, multiple dose pen injectors may optionally include a design feature which provides end of injection indication to the user such as a visual feature wherein the dose set knob position & dose markings return to zero/starting position or an audible feature wherein the clicking stops at end of injection. The multiple dose pen injection device thus improves accuracy of dose delivery and ease of use for self-injection. Advantageous properties include portability and ease of reading, ease of dose adjustment, ergonomic design and sturdiness.

In one specific embodiment of the present invention, the sterile solution is provided in a multiple dose pen type of injection device, where the multiple dose pen injector consists of a cartridge made up of a USP Type-I Siliconised glass having a specific dimensions viz, total height of 62.30±0.15 mm, body diameter of 11.65±0.15 mm, neck outer diameter of 7.15±0.2 mm, bore diameter of 3.15±0.15 mm and collar thickness of 2.90±0.1 mm. Further the multiple dose pen injector is stoppered with a 10 mm Red Bromobutyl 4023/50 Wester 2223 Sil 4 RFS plunger stopper. Plunger stopper has specific dimensions as outer diameter is 10.0±0.15 mm and total height of 8.13±0.3 mm. Furthermore, the stoppered glass cartridge is sealed with a Combination RFS Wester Seal of Bromobutyl rubber 4780/40 Cram/Outer 7778/40 Gray having dimensions as, outer diameter of 7.66±0.54 mm, inner diameter is 7.5+0.1, −0 and total height of 5.3+0.1, −0.2. Without wishing to be bound by any theory, inventors of the present invention believes that the sterile solution of the leuprolide acetate is stable in the cartridge with plunger stopper and Combiseal.

According to one embodiment of the present invention, the sterile solution of leuprolide acetate can be prepared by the following process which involves—

(i) solubilization of preservative in specified volume of water for injection at a temperature of 20° C. to 25° C. under stirring, followed by addition and dissolution of specified quantity of sodium chloride under stirring until a clear solution was obtained.

(ii) addition of Leuprolide acetate slowly into above solution with continuous stirring to ensure complete dissolution of leuprolide acetate followed by adjustment of the pH of the solution to about 4.50 to 6.00 using sufficient quantity of 10% glacial acetic acid.

(iii) Sterilization of pharmaceutical solution of leuprolide acetate by membrane filtration using 0.45 micron PVDF pre-filter and 0.2 micron filter; followed by aseptic filling of the solution under laminar flow into pre-sterilized cartridges.

In this embodiment, the cartridges were first pre sterilized by an appropriate process and then the solutions were filled aseptically under laminar flow. The material of construction of the cartridge can be either glass or plastic. Depending upon the material, a suitable sterilization process can be adapted.

In another aspect, the present invention provides a method of administration of leuprolide acetate to a subject in need thereof, said method comprising daily subcutaneous administration of solution of leuprolide acetate to the subject, wherein the solution is administered directly from the multiple dose pen injection device. This may be of particular importance in case of administration in children, where individualization for each child is necessary and the dose is based on mg/kg ratio of drug to body weight. The multiple dose pen injection device of the present invention imparts flexibility in terms of selecting & administering varied doses of the medicament as well as the convenience of self administration. The device thus provides an accurate and convenient method of administration of leuprolide acetate which is not available in the art.

The invention also provides a method of maintaining the sterility of a reservoir of a leuprolide acetate solution in a multiple dose pen injection device for subcutaneous injection of the solution to a subject in multiple doses from the reservoir, the method comprising providing in a multiple dose pen injection device a solution containing at least 10 mg/ml of leuprolide acetate and a preservative at concentration ranging from the concentration at which 5 mg/ml of leuprolide acetate is maintained sterile to 1.25 times that concentration of the preservative and whereby the solution is exposed to non-sterile conditions due to multiple doses being administered from the reservoir.

The recommended starting dose is 50 μg/kg/day administered as a single subcutaneous injection, which can be conveniently given with the help of the injection device of the present invention. In one embodiment, the multiple dose pen injector device includes a dose dialing facility with markings of 0, 250, 500, 750, 1000 indicating dose in μg such that the desired dose can be administered through variable volumes ranging from 10 μL to 200 μL, preferably 25 μL to 100 μL. Alternatively the markings on the dose dial can be represented in terms of mg dose, wherein the markings may include '0.0 mg' and '1.0 mg' representing the initial position and 1.0 mg dosing position respectively.

The multiple dose pen injection device of the present inventions improves accuracy of dose delivery and ease of use for self-injection. For administering the drug through the multiple dose pen injection device the user has to attach a new needle on the tip of the cartridge holder, prime the multiple dose pen prior to first use, select the dose and inject the drug by pushing the release button. The dose dialing facility enables the priming of multiple dose pen injector prior to first use, where the dose set knob is set to the appropriate priming unit (P) on the dose dial and the pressing of release button until a stream of medication oozes out from the needle to ensure the removal of any air bubble inside the cartridge. Once the priming is done, the dose to be administered is selected on the dose dial and the drug is injected by pushing the release button.

The following examples illustrate the scope of the present invention, without any limitation thereto.

EXAMPLE 1-2

The sterile solution of the present invention is prepared according to the formula described in Table 1.

TABLE 1

| | | Sterile solution of leuprolide acetate according to present invention | | | |
| --- | --- | --- | --- | --- | --- |
| | | Example 1 | | Example 2 | |
| Sr. No. | Ingredients | Concentration | Amount per dose | Concentration | Amount per dose |
| 1 | Leuprolide acetate | 5.0 mg/ml | 1.0 mg | 10.0 mg/ml | 1.0 mg |
| 2 | Sodium chloride | 6.3 mg/ml | 1.26 mg | 6.3 mg/ml | 0.63 mg |
| 3 | Benzyl alcohol | 9.0 mg/ml | 1.8 mg | 11.25 mg/ml | 1.125 mg |
| 4 | Water for | q.s to 2.8 ml | q.s to 0.2 ml | q.s. to 2.8 ml | q.s to 0.1 ml |

TABLE 1-continued

Sterile solution of leuprolide acetate according to present invention

| Sr. No. | Ingredients | Example 1 | | Example 2 | |
|---|---|---|---|---|---|
| | | Concentration | Amount per dose | Concentration | Amount per dose |
| | injection | | (single dose volume) | | (single dose volume) |
| 5 | Glacial Acetic acid | q.s to adjust pH between 4.50 to 6.00 | q.s to adjust pH between 4.50 to 6.00 | q.s. to adjust pH between 4.50 to 6.00 | q.s. to adjust pH between 4.50 to 6.00 |
| Pack style | 3.0 ml multiple use cartridges with multiple dose pen injector device having dose dialing facility | | | | |

A solution was prepared using 80% of benzyl alcohol (80% of 9 mg/ml) that is used in Lupron® but with 10 mg/ml of leuprolide acetate instead of 5 mg/ml of leuprolide acetate. In order to check whether the solution would remain preserved throughout the shelf life, the lowest permissible concentration i.e (80-120%) of 9 mg per ml, which is 7.2 mg/per was used. The solution was subjected to preservative efficacy test.

TABLE 2

Solution of comparative example

| Sr. No. | Ingredients | Comparative Example | |
|---|---|---|---|
| | | Solution Concentration | Amount per 1 mg dose |
| 1 | Leuprolide acetate | 10.0 mg/ml | 1.0 mg/dose |
| 2 | Sodium chloride | 6.3 mg/ml | 0.63 mg/dose |
| 3 | Benzyl alcohol | 7.2 mg/ml (80% of 9 mg/ml as per Lupron ®) | 0.72 mg/dose |
| 4 | Water for injection | q.s. to 2.8 ml | q.s. to 0.1 ml (single dose volume) |
| 5 | Glacial Acetic Acid | q.s. to adjust pH between 4.50 to 6.00 | q.s. to adjust pH between 4.50 to 6.00 |
| Pack style | 3.0 ml multiple use cartridges with multiple dose pen injector device having dose dialing facility | | |

Method of preparation: Specified volume water for injection was collected in suitable container at a temperature of 20° C. to 25° C. To this, a specified quantity of benzyl alcohol was added under stirring to form a clear solution. Specified quantity of sodium chloride was dissolved in above solution under stirring until the clear solution was obtained. Leuprolide acetate was added slowly into above solution of benzyl alcohol and sodium chloride with continuous stirring to ensure complete dissolution of leuprolide acetate. Further, the pH of the solution was adjusted to about 4.50 to 6.00 with sufficient quantity of 10% glacial acetic acid. This unfiltered bulk solution was stored under nitrogen blanket until before subjecting to membrane filtration. The bulk solution of leuprolide acetate was sterilized by aseptic filtration through 0.45 micron PVDF pre-filter and 0.2 micron PVDF filter and filtered solution was stored under nitrogen blanket. Finally pre-sterilized cartridges were filled aseptically with bulk solution with standard fill volume and stoppered.Preservative efficacy test (PET) was carried out on the sterile solutions as per United States Pharmacopoeia, <51>, Antimicrobial Effectiveness Testing, USP34, pp 48-50. It was found that even at a higher concentration of leuprolide acetate, that is at 10 mg per ml strength, 11.25 mg per ml of benzyl alcohol was sufficient to preserve the solution. However, when the benzyl alcohol was present at a concentration of 7.2 mg per ml, the solution was not sterile and did not pass the preservative efficacy test.

The results of the preservative efficacy test unexpectedly revealed that 7.2 mg/ml of benzyl alcohol (which is 80% of 9 mg/ml) was not efficacious to preserve the solution, which is apparent from the fact that the solution did not pass the preservative efficacy test. Further, the concentration of the benzyl alcohol when increased from 9 mg/ml to 11.25 mg/ml, this amount of preservative was sufficient to provide sterility. Therefore, the sterile solution of comparative example is not according to the present invention which is to provide a sterile solution comprising leuprolide acetate in a pharmaceutically acceptable vehicle, wherein solution is present as a reservoir in a multiple dose pen injection device, the device being adapted to subcutaneously inject a portion of the said reservoir in a single daily dose and further being adapted to provide multiple portions of the said solution, while the reservoir remains sterile.

At 7.2 mg of benzyl alcohol which is 80% of the labeled amount of preservative, the solution was not remaining sterile, throughout the shelf life of the multiple dose pen injection device.

EXAMPLE 3

The in use stability study of multiple dose pen device having Leuprolide Acetate solution at a concentration of 10 mg/ml was performed by three type of tests,—(A) Physical; (B) Chemical and (C)Microbiological (sterility) tests.

Leuprolide Acetate Injection Solution having concentration of 10 mg/mL was prepared as per Example 2. 2.8 ml of the solution was aseptically filled in the 3 ml colorless USP type-I siliconised glass cartridge of the multiple dose pen device having a RFS Wester seal and Bromobutyl 4023/50 Wester 2223 Sil 3 Rfs Plunger Stopper. For withdrawal of each dose of the solution, a sterile needle (31 gauge, 5 mm-12.7 mm) was attached to the multiple dose pen and 0.05 ml of solution was withdrawn once daily for 28 consecutive days. Remaining amount of solution in the cartridge at the end of 28 days (about 1.4 ml) was tested for Physical; Chemical and Microbiological (sterility) evaluation.

(A) The physical evaluation included analysis of parameters like physical appearance such as clarity of solution, presence of particulate matter, pH of the solution.

(B) Chemical evaluation included assay of Leuprolide Acetate and assay of Benzyl Alcohol. The results of these physical and chemical parameters are tabulated in Table 3.

TABLE 3

Results for in-use physical and chemical test parameters:

| S. No. | Test Parameters | Initial observation | Observation after 28 days of withdrawal of daily dose |
|---|---|---|---|
| 1 | Description | Clear colorless solution free from visible particulate matter | Clear colorless solution free from visible particulate matter |
| 2 | pH | 4.86 | 4.75 |
| 3 | Absorbance (at 420 nm) | 0.019 AU | 0.025 AU |
| 4 | Percent Transmittance at 650 nm | 99.731% | 98.509% |
| 5 | Leuprolide Acetate Assay by LC | 104.42% | 105.71% |
| 6 | Benzyl Alcohol Assay by LC | 99.93% | 99.23% |

It can be seen from the results in Table 3 that the pharmaceutical solution of the present invention remained clear, colorless and free from visible particulate matter at the end of 28 days. The pH was found to remain unchanged. The pharmaceutical solution of leuprolide acetate remained physically and chemically stable in the multiple dose pen device despite presence of concentrated solution of leuprolide acetate. This is evident from the assay values of Leuprolide acetate and Benzyl alcohol that did not changed substantially as compared to the initial values. Also the values were within the specified limits at the end of 28 day in-use testing period. Based on the observation that no substantial change in the assay values of benzyl alcohol and leuprolide acetate occurs after 28 days, it can be concluded that the preservative used (benzyl alcohol) in an amount of 9.0 to 11.25 mg/ml did not react with either the drug (i.e. Leuprolide acetate) or with the components of the container or closure system, and it is stable and active for the shelf life of the product.

(C) Microbiological Testing

Two parameters were tested as per the procedure given in United States Pharmacopoeia (USP)

(1) Test for Sterility and (2) Bacterial Endotoxin Test, (1) Test for Sterility—The test was performed as per United States Pharmacopoeia (USP), chapter <71>, Sterility Tests, USP34, pp 65-70. The sample was incubated in Soyabean Casein Digest Medium and Fluid Thioglycolate Medium for 14 days and the growth of microorganisms, if any was observed. The observations are presented in Table 4 below:

TABLE 4

Observations for Test for Sterility

| | | DAY | | | | | | | | | | | | | |
|---|---|---|---|---|---|---|---|---|---|---|---|---|---|---|---|
| S. No. | Medium | 1 | 2 | 3 | 4 | 5 | 6 | 7 | 8 | 9 | 10 | 11 | 12 | 13 | 14 |
| 1 | Fluid Thioglycolate | N | N | N | N | N | N | N | N | N | N | N | N | N | N |
| 2 | Soyabein Casein digest | N | N | N | N | N | N | N | N | N | N | N | N | N | N |

N—No Microbial Growth Observed
G—Growth Observed

It can be seen from the results in Table 4 that no growth of microorganisms was observed after 14 days of incubation period. These test results indicate that the sample solution remained sterile even after 28 days 'in-use' of the multiple dose pen injection device.

(2) Bacterial Endotoxins Test (BET)—Bacterial Endotoxins Test was performed as per the United States Pharmacopoeia (USP), chapter <85>, using gel clot technique. It was observed that the test sample complied with the specification and passed the test. Satisfactory Bacterial Endotoxin levels indicated that there was no ingress of microbes during the repeated multiple use of the multiple dose pen injector device throughout its in-use shelf life (28 days). The BET studies also indicated effective closure system of the device. This is because there was no endotoxin formation indicating absence of any killed microbial cells that might have been killed due to the effective preservative like benzyl alcohol.

Based on the observations of the physical, chemical and microbiological tests as described above, it can be concluded that the pharmaceutical solution of leuprolide acetate of the present invention remained sterile as well as physically and chemically stable in the multiple dose pen device throughout the storage and in-use shelf-life of the product, despite presence of concentrated solution of leuprolide acetate. The pharmaceutical solution of the present invention maintained adequate sterility during the in-use shelf life and no microbial contamination occurred even after repeated withdrawal of the dose continuously from day 1 to day 28.

EXAMPLE 4

Storage stability testing—The pharmaceutical solution of example 2 contained in the multiple dose pen injector device was subjected to stability studies at accelerated storage conditions of 40° C./75% RH for a period of 3 months. In this storage period, the device was not used i.e. no solution was withdrawn and the cartridge was not punctured. The solution was analyzed for the assay of Leuprolide acetate and benzyl alcohol as well as for related substances. The results are tabulated in the table 5 below.

TABLE 5

Observation for stability studies of the leuprolide acetate multiple dose pen injector at initial and on storage condition of 40° C./75% RH for 3 months

| Test | Initial | 40° C./75% RH for 3 Months |
|---|---|---|
| | Assay | |
| Leuprolide acetate | 105.26 | 106.32 |
| Benzyl alcohol | 101.54 | 104.61 |

TABLE 5-continued

Observation for stability studies of the leuprolide acetate multiple dose pen injector at initial and on storage condition of 40° C./75% RH for 3 months

| Test | Initial | 40° C./75% RH for 3 Months |
|---|---|---|
| Related substances (%) | | |
| PGlu-His-Trp-OH | 0.055 | 0.263 |
| Des-pGlu-Leuprolide | 0.212 | 0.791 |
| Impurity A (NMT 0.5) | 0.049 | 0.079 |
| Impurity B (NMT 0.5) | 0.069 | 0.225 |
| Impurity C (NMT 0.5) | 0.023 | Not detected |
| Impurity D (NMT 0.5) | 0.024 | Not detected |
| Unknown Impurities | | |
| Highest unknown impurity (NMT 0.5) | 0.156 | 0.287 |
| Total impurities (NMT 2.5) | 1.241 | 2.436 |

The observations of the aforesaid accelerated stability tests indicated that the solution stored in the multiple dose pen injection device when kept at room temperature or accelerated stability condition such as 40° C./75% RH for 3 months, remains stable, in terms of both the assay of leuprolide as well as assay of benzyl alcohol, and the related substance/impurities remained within limits, thus indicating that the pharmaceutical solution of the present invention in the multiple dose pen injector device remains stable on storage throughout the shelf life of the product.

We claim:

1. A multiple dose leuprolide acetate pen injection device containing a sterile solution comprising leuprolide acetate in an amount of 10 mg per ml of the solution and at least one preservative in a pharmaceutically acceptable vehicle in an amount sufficient to maintain sterility of the solution throughout the shelf life of the sterile solution, wherein:

the solution is present as a reservoir in the multiple dose pen injection device, the device being adapted to subcutaneously inject a portion of the reservoir to provide a single daily dose of leuprolide and the device further being adapted to inject multiple portions of the solution while the reservoir remains sterile, wherein the multiple dose pen injection device is configured to administer 10 to 200 microliters of the solution to provide the single daily dose of leuprolide, and wherein the at least one preservative includes benzyl alcohol present in a concentration of 11.25 mg per ml of the solution.

2. The sterile solution as claimed in claim 1 wherein the reservoir contains 28 doses.

3. A multiple dose leuprolide acetate pen injection device containing a sterile solution comprising leuprolide acetate in an amount of 10 mg per ml of the solution and at least one preservative in a pharmaceutically acceptable vehicle in an amount sufficient to maintain sterility of the solution throughout the shelf life of the sterile solution, wherein:

the solution is present as a reservoir in the multiple dose pen injection device, the device being adapted to subcutaneously inject a portion of the reservoir to provide a single daily dose of leuprolide and the device further being adapted to inject multiple portions of the solution while the reservoir remains sterile, wherein the multiple dose pen injection device is configured to administer 10 to 200 microliters of the solution to provide the single daily dose of leuprolide, and wherein the solution remains stable when kept at 40° C/75% RH for 3 months.

4. The sterile solution as claimed in claim 3 wherein the reservoir contains 28 doses.

* * * * *